United States Patent
He et al.

(10) Patent No.: US 9,933,357 B1
(45) Date of Patent: Apr. 3, 2018

(54) ELLIPOSOMETER SYSTEM WITH POLARIZATION STATE GENERATOR AND POLARIZATION STATE ANALYZER IN ENVIRONMENTAL CHAMBER

(71) Applicant: J.A. WOOLLAM CO., INC., Lincoln, NE (US)

(72) Inventors: Ping He, Lincoln, NE (US); Gregory K. Pribil, Lincoln, NE (US); Martin M. Liphardt, Lincoln, NE (US)

(73) Assignee: J. A. WOOLLAM CO., INC., Lincoln, NE (US)

( * ) Notice: Subject to any disclaimer, the term of this patent is extended or adjusted under 35 U.S.C. 154(b) by 0 days.

(21) Appl. No.: 15/530,584

(22) Filed: Feb. 3, 2017

Related U.S. Application Data

(60) Provisional application No. 62/389,395, filed on Feb. 25, 2016.

(51) Int. Cl.
*G01N 21/21* (2006.01)

(52) U.S. Cl.
CPC ..... *G01N 21/211* (2013.01); *G01N 2201/023* (2013.01); *G01N 2201/0227* (2013.01); *G01N 2201/084* (2013.01)

(58) Field of Classification Search
CPC .................................................. G01N 21/211
USPC ....................................................... 356/364
See application file for complete search history.

(56) References Cited

U.S. PATENT DOCUMENTS

| | | |
|---|---|---|
| 5,929,995 A | 7/1999 | Johs |
| 6,636,309 B1 | 10/2003 | Johs et al. |
| 6,940,595 B1 | 9/2005 | Johs et al. |
| 6,982,792 B1 | 1/2006 | Woollam et al. |
| 7,026,626 B2 | 4/2006 | Harrison |
| 7,030,982 B1 | 4/2006 | Woollam et al. |
| 7,158,231 B1 | 1/2007 | Woollam et al. |
| 7,193,708 B1 | 3/2007 | Herzinger |
| 7,209,234 B2 | 4/2007 | Woollam et al. |
| 7,253,900 B1 | 8/2007 | Woollam et al. |
| 7,274,450 B1 | 9/2007 | Green et al. |
| 7,283,234 B1 | 10/2007 | Woollam et al. |
| 7,304,713 B2 | 12/2007 | Yi |
| 7,336,361 B1 | 2/2008 | Liphardt et al. |
| 7,394,551 B2 | 7/2008 | Harrison |
| 7,426,030 B1 | 9/2008 | Liphardt et al. |
| 7,616,319 B1 | 11/2009 | Woollam et al. |
| 7,633,625 B1 | 12/2009 | Woollam et al. |
| 7,746,471 B1 | 6/2010 | Johs et al. |
| 8,014,000 B2 | 9/2011 | Harrison |
| 8,054,453 B2 | 11/2011 | Harrison |
| 8,248,606 B1 | 8/2012 | Liphardt et al. |
| 2002/0024668 A1* | 2/2002 | Stehle .................. G01N 21/211 356/369 |
| 2005/0254050 A1* | 11/2005 | Fielden .................... G01J 3/10 356/369 |
| 2011/0109906 A1* | 5/2011 | Liphardt ................ G01N 21/01 356/400 |

* cited by examiner

*Primary Examiner* — Tarifur Chowdhury
*Assistant Examiner* — Omar Nixon
(74) *Attorney, Agent, or Firm* — James D. Welch

(57) ABSTRACT

An ellipsometer system with polarization state generator and polarization state analyzer components inside at least one internal environment supporting encasement, said at least one encasement being present inside said environmental chamber.

10 Claims, 5 Drawing Sheets

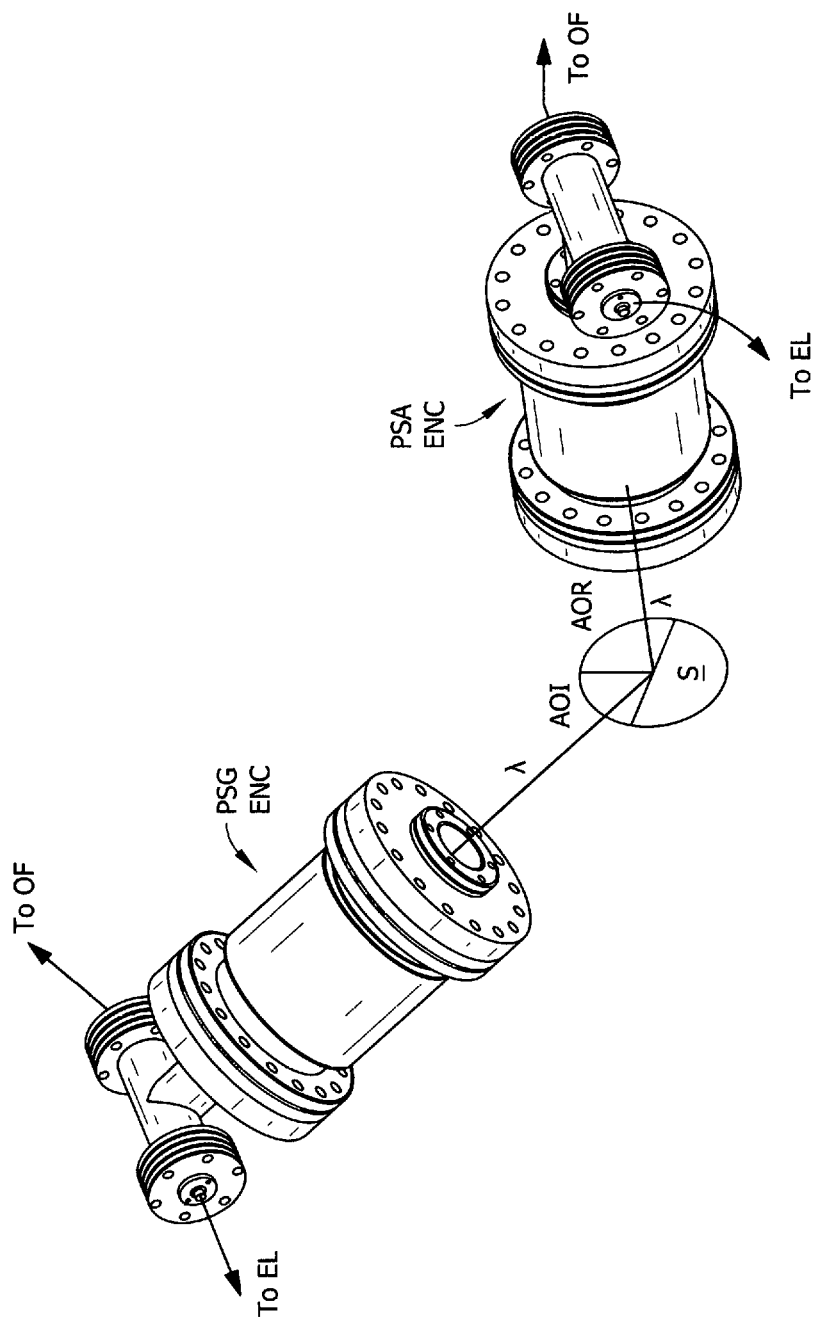

ELLIPOSOMETER SYSTEM WITH POLARIZATION STATE GENERATOR AND POLARIZATION STATE ANALYZER IN ENVIRONMENTAL CHAMBER

This Application Claims benefit of Provisional Application No. 62/389,395, Filed Feb. 25, 2016.

TECHNICAL FIELD

The present invention relates to the application of ellipsometer and the like systems to investigate samples inside an environmental chamber, (eg. vacuum chamber), and more particularly to an ellipsometer system that preferably places polarization state generator and polarization state analyzer components inside at least one internal environment supporting encasement, said at least one encasement being present inside said environmental chamber.

BACKGROUND

It is well known to investigate samples present inside an environmental chamber, (eg. a vacuum chamber or a chamber filled with a gas), by causing the ellipsometer or the like system to be entirely present outside said environmental chamber, so that an electromagnetic beam generated by a polarization state generator is directed to pass through a first transparent window in said environmental chamber, interact with said sample therewithin, then pass through a second transparent window in said environmental chamber and enter the polarization state analyzer, which passes the electromagnetic beam to a detector thereof. Such a system is described in U.S. Pat. No. 7,253,900 to Woollam et al., for instance. Problems exist when said approach is practiced, however, in that the structure of an environmental chamber can prevent placing polarization state generator and polarization state analyzer components close to a sample under investigation. This can limit the ability to effect an intended, (eg. small and circular), beam spot at the sample location. To provide better proximity of polarization state generator and polarization state analyzer components to a sample under investigation it would be beneficial to be able to place at least some of an ellipsometer or the like components inside an environmental chamber. Beam directing optics can be placed inside an environmental chamber, (see U.S. Pat. No. 5,929,995), to overcome some inherent problems, but this is sometimes not sufficient to provide an electromagnetic beam spot of a certain size and shape onto a sample inside said environmental chamber. Placing polarization state generator and polarization state analyzer components inside an environmental chamber very near an investigated sample can aid with achieving more optimum results in this regard. Therefore, it would be of value to be able to place actual ellipsometer polarization state generator and polarization state analyzer components inside an environmental chamber. Doing so, however, can subject polarization state generator and polarization state analyzer components to, for instance, a vacuum or a gas, and such can be detrimental to their operation. Further, the presence of said components in an environmental chamber can prevent vacuum formation by outgassing.

It is disclosed that the J.A. Woollam Co. has previously obtained many Patents for ellipsometer and the like systems applied with environmental chambers. See for example U.S. Pat. Nos. 5,929,995, 6,636,309, 6,940,595, 6,982,792, 7,030,982, 7,158,231, 7,193,708, 7,209,234, 7,274,450, 7,253,900, 7,283,234, 7,336,361, 7,426,030 and 7,746,471.

In particular, the 231 patent discloses placing an entire ellipsometer system inside an environmental chamber in FIGS. 1d, 3 and 5a, and the 792 patent indicates a similar scenario in FIG. 1b. The present invention is distinguished in that, while ellipsometer system polarization state generator and polarization state detector components are contained within an environmental chamber, they are present in encasements that provide components therewithin with an atmosphere that is conducive to their optimum operation. Also, the present invention preferably maintains the source and detector of electromagnetic radiation outside the environmental chamber and provides access via port couplers.

Additional known Patents, not believed to be particularly relevant, are: U.S. Pat. Nos. 8,248,606; 8,054,453; 8,014,000; 7,633,625; 7,616,319; 7,394,551; 7,336,361; 7,304,713; 7,253,900; 7,158,231 and 7,026,626.

Need remains for an ellipsometer system, at least some of the components of which can be placed in an environmental chamber while protecting said components against the effects of, for instance, a vacuum environment.

DISCLOSURE OF THE INVENTION

The Present Invention comprises an environmental chamber and ellipsometer system, wherein the ellipsometer system comprises:
   a) a source of a beam of electromagnetic radiation;
   b) polarization state generator components;
   c) polarization state analyzer components;
   d) a detector of electromagnetic radiation.

In use a beam of electromagnetic radiation from the source thereof is caused to pass through said polarization state generator components and then continue on to interact with a sample, then pass through the polarization state analyzer components and enter said detector of electromagnetic radiation, wherein data is produced which can be analyzed to characterize the sample.

Said combined environmental chamber and ellipsometer system is distinguished in that the polarization state generator and polarization state analyzer components are present inside at least one encasement, which at least one encasement is present inside said environmental chamber.

The combined environmental chamber and ellipsometer system can comprise two encasements inside said environmental chamber, one of which contains polarization state generation components, and the other of which contains polarization state analyzer components. This is a preferred embodiment.

Said source of a beam of electromagnetic radiation and said detector of electromagnetic radiation provide and receive, respectively, electromagnetic radiation to and from said polarization state generator and polarization state analyzer components, respectively, via fiber optics through at least one sealed port coupler in said environmental chamber.

At least one of said polarization state generation components and/or said polarization state analyzer components can be electrically operated, and electrical energy is provided thereto through at least one sealed port coupler in said environmental chamber.

There preferably are separate sealed port couplers present for optical fibers and electrical energy transmitting wires to said polarization state generation components and/or said polarization state analyzer components.

Said at least one encasement present inside said environmental chamber, typically supports a pressure or a gas, (and optionally temperature via electrical means), internal thereto which is different from that inside the environmental chamber in which said encasement(s) is/are present. This is to enable more optimum operation of components therewithin. Polarization state generator or polarization state analyzer components are typically designed for application at room atmospheric pressure, and temperature. Positioning said components in an environmental chamber, where pressure or atmosphere composition, for instance, is not at room ambient, can cause less than optimal operation of said components.

The present invention system can provide that said at least one encasement present inside said environmental chamber allows for "Z", and "X" and/or "Y" motion over an area of said sample, and said sample being investigated is movable in the "Y" and/or "X" direction respectively, thereby allowing for sample mapping at a multiplicity of "X" and/or "Y" locations on said sample, where "Z" indicates a distance between said sample and said polarization state generation and said polarization state analyzer components.

Said polarization state generator components and polarization state analyzer components typically each comprise a polarizer, (sometimes termed an analyzer in the polarization state analyzer system). It is also noted that the polarizer and analyzer can preferably be remotely controlled to allow setting of its azimuthal angle, so that it outputs polarized electromagnetic radiation with "p" or "s" polarization, or at some angle therebetween. Present compensator(s) in the polarization state generator and polarization state analyzer can be likewise electrically controlled to set azimuthal angles thereof. Note that said polarization state generator components and polarization state analyzer components each comprises a polarizer, and at least one thereof can also comprise a compensator.

A method of mapping a sample comprising the steps of:
a) providing a combined environmental chamber and ellipsometer system as described above;
b) for each of a plurality of "X", "Y" and "Z" values causing a beam of electromagnetic radiation from said source of a beam of electromagnetic radiation to pass through said polarization state generator components and then continue on to interact with a sample, then pass through the polarization state analyzer components and enter said detector of electromagnetic radiation, wherein data is produced which can be analyzed to characterized the sample; and
c) for each of said plurality of "X", "Y" dud "Z" values analyzing the data produced by said detector to provide insight to said sample at a multiplicity of mapped locations thereon.

The present invention is characterized primarily by the presence of polarization state generation and polarization state analyzer components being present in at least one encasement that supports an internal pressure or gas, and optionally temperature, wherein said at least one, (preferably two), encasement(s) is present inside an environmental chamber and provides an environment therewithin that is different than that present inside said environmental chamber. A major advantage of placing polarization state generation and polarization state analyzer components inside an environmental chamber is that they can be placed in closer proximity to a sample than is otherwise possible, and that enables better control of a beam spot size and shape at the sample location.

The present invention will be better understood by reference to the Detailed Description Section of this Specification, in combination with the Drawings.

BRIEF DESCRIPTION OF THE DRAWINGS

FIG. 2F is included to better indicate that the encasements for the present invention polarization state generator and the polarization state detector components are sealed so that a pressure can be maintained therewithin that is compatible with their operation.

DETAILED DESCRIPTION

Figure 1A:
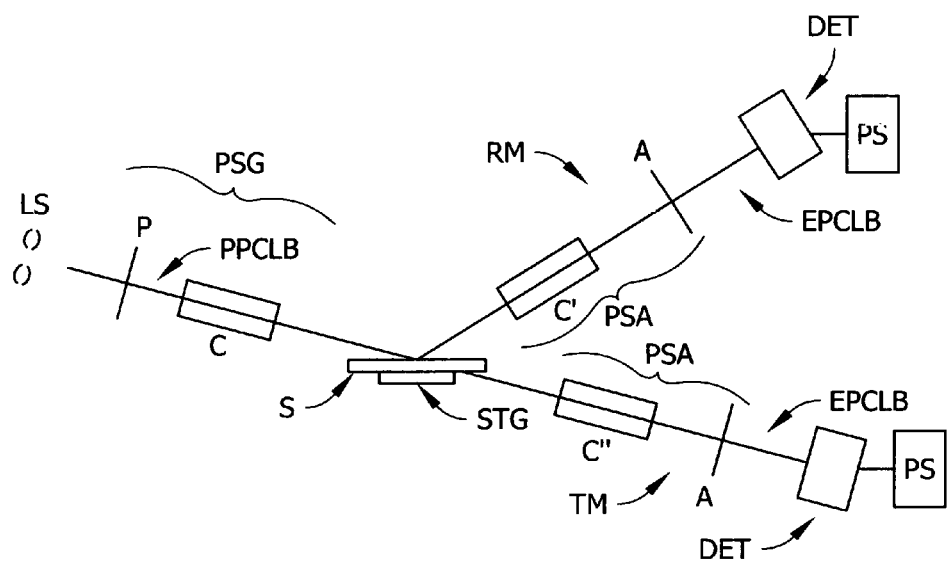
FIG. 1A shows a prior art ellipsometer system, that demonstrates both reflection and transmission sample investigation options.
Figure 1B:
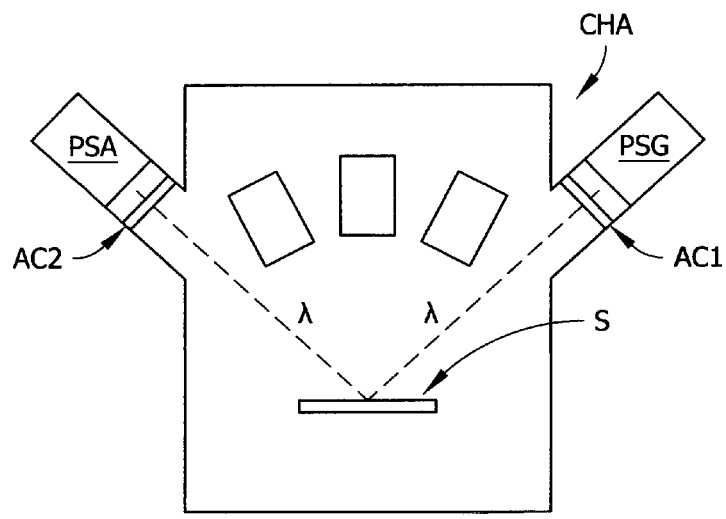
FIG. 1B shows an environment chamber, wherein all FIG. 1A ellipsometer components are all outside the chamber, and only a beam of electromagnetic radiation (λ) enters thereinto via an input window, interacts with a sample and exits via an output window.

Turning now to the Drawings, FIG. 1A shows a prior art ellipsometer system demonstrating both reflection and transmission modes of sample investigation operation. Present are a source (LS) of a beam of electromagnetic radiation, a Polarizer (P) a compensator (C), a sample (S), additional possibly present compensator (C') (C"), analyzer (A), detector (DET), and an analysis system (PS) that accepts data from the detector (DET) and analyzes it, (after the sample (S) components are shown in both reflection and transmission legs). Note that (PPCLB) and (EPCLB) are polarized electromagnetic beams before and after the sample (S). FIG. 1B shows a prior art system comprising an ellipsometer system as in FIG. 1A, and an environment chamber (CHA), wherein all ellipsometer components (PSG) (PSA) are outside the chamber (CHA), and only a beam ( ) of electromagnetic radiation enters thereinto via an input window (AC1), interacts with a sample (S) and exits an output window (AC2). Note, all pre- and post-sample (S) components in FIG. 1A are, for the purposes of FIG. 1B, included in the FIG. 1B (PSG) and (PSA) and all thereof are outside the environmental chamber (CHA), sequestered by (AC1) and (AC2).

Figure 2A:
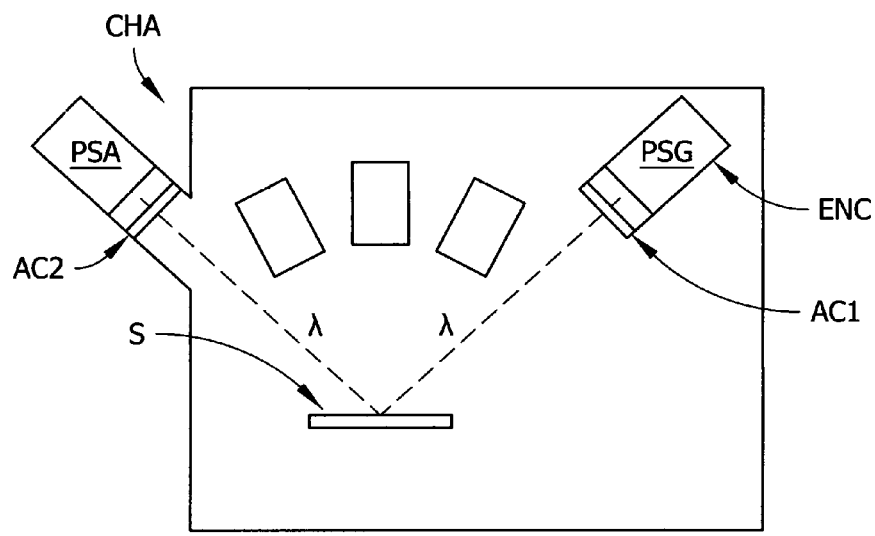
FIG. 2A shows a present invention polarization state generator inside an environmental chamber and polarization state detector outside said environmental chamber.

FIG. 2A shows a present invention polarization state generator (PSG) inside an environmental chamber (CHA) and polarization state detector (PSA) outside said environmental chamber (CHA).

Figure 2B:
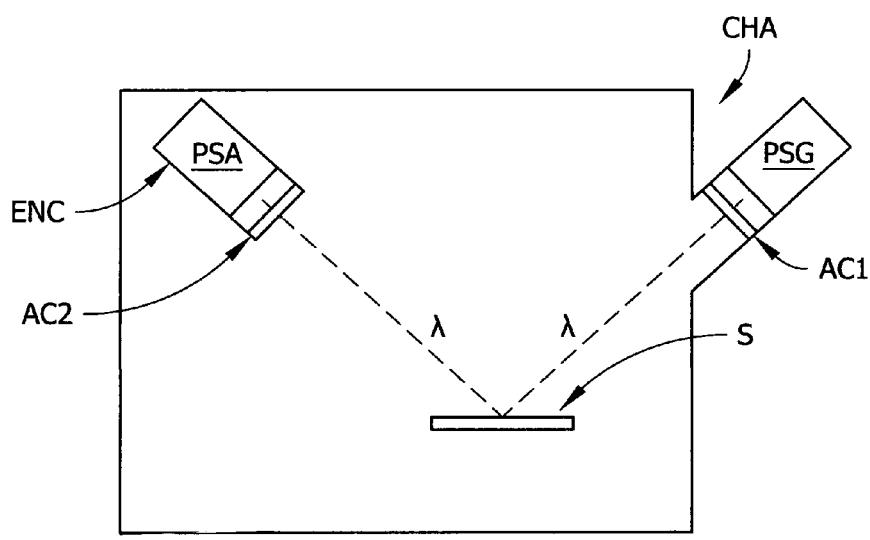
FIG. 2B shows a present invention polarization state generator outside an environmental chamber and polarization state detector inside an environmental chamber.

FIG. 2B shows a present invention polarization state generator (PSG) outside an environmental chamber (CHA) and polarization state detector (PSA) inside an environmental chamber (CHA).

In both FIGS. 2A and 2B the polarization state generator or analyzer present inside the environmental chamber are in an encasement that allows controlling the pressure, and optionally temperature, to which the components therewithin are subject.

Figure 2C:
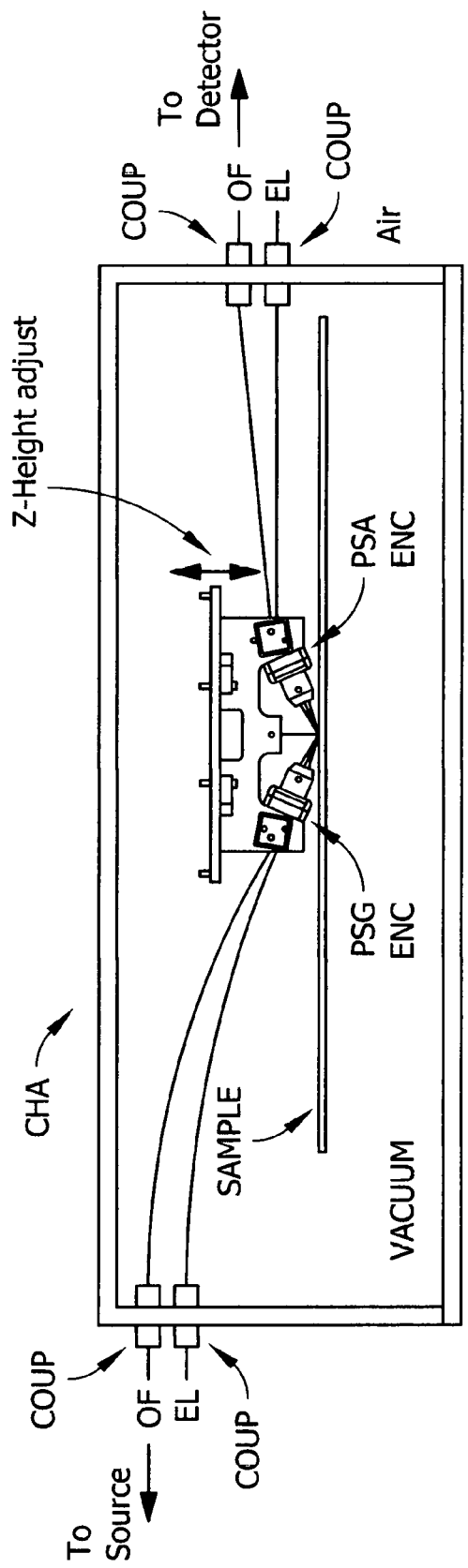
FIG. 2C shows a preferred present invention that comprises a polarization state generator and a polarization state detector, both inside an environmental chamber.

FIG. 2C shows both a present invention polarization state generator (PSG) and polarization state detector (PSA) inside an environmental chamber (CHA), both being present in separate encasements (ENC). This is a preferred embodiment. Note that access to source and detector is via light fibers (LF) via port couplers (COUP), as is electrical (EL) input which can be used to operate the (PSG) and (PSA) components.

Figure 2D:
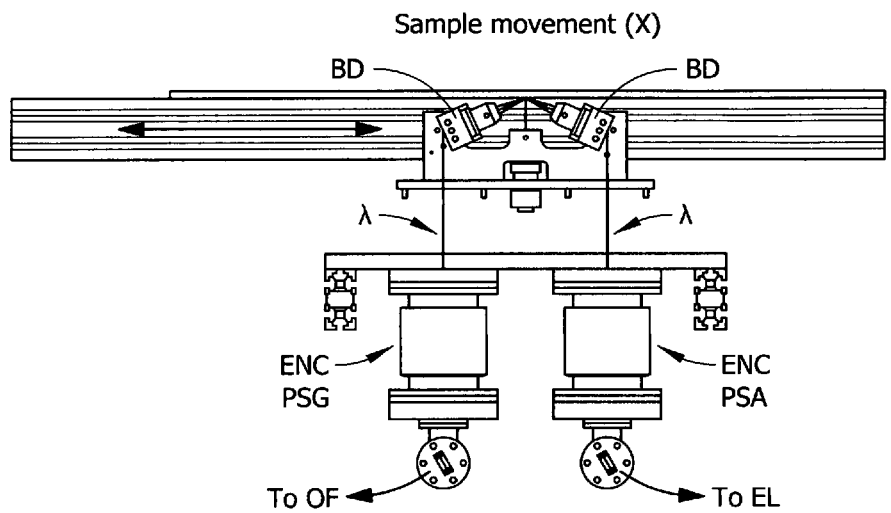
FIG. 2D show present invention polarization state generator and polarization state detector encasements as part of a system for enabling sample movement.

FIG. 2D shows a present invention polarization state generator (PSG) and polarization state detector (PSA) encasements (ENC) as part of a system for allowing sample movement in an "X" direction. Note that FIG. 2D also shows beam directors (BD) that handle incident and reflected electromagnetic beams toward and from a sample, respectively. While not required by the present invention, beam directors (BD), as shown, can enable more convenient orientation of comparatively more bulky polarization state generator (PSG) and polarization state detector (PSA) encasements (ENC) in an environmental chamber (CHA), than is possible in the configuration of FIG. 2C.

Figure 2E:
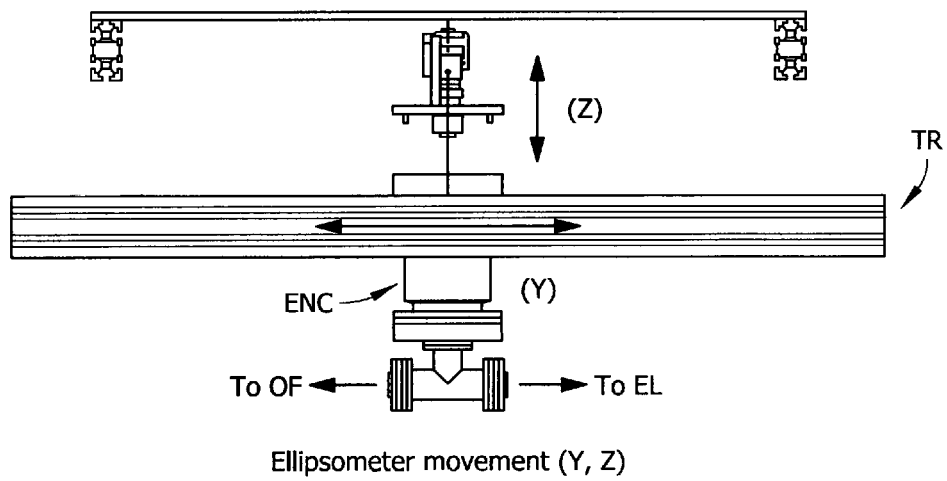
FIG. 2E shows a present invention polarization state generator or polarization state detector encasement as part of a system for allowing ellipsometer and sample movement.

FIG. 2E shows a present invention polarization state generator (PSG) or polarization state detector (PSA) encasement (ENC) as part of a system for allowing sample movement in "Y", and ellipsometer movement in "Z" directions.

FIG. 2F is included to better indicate that the encasements (ENC) for the present invention polarization state generator (PSG) and the polarization state detector (PSD) components are sealed so that a pressure can be maintained therewithin that is compatible with their operation. Components in a (PSG) or (PSA) are typically operated near atmospheric pressure, (as indicated in FIGS. 1A and 1B). While atmospheric pressure is not an absolute requirement, placing said components designed to operate at atmospheric pressure, in a vacuum can cause components of a (PSG) or (PSA) to operate other than as expected, or not at all. The present invention minimizes such problems by using encasements (ENC), that allow setting a desired pressure or gas composition, (and optionally temperature), inside thereof.

It is noted that Stainless Steel is a preferred material for the outer surface of the encasements (ENC).

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

The invention claimed is:

1. A combined environmental chamber and ellipsometer system, wherein the ellipsometer system comprises:
   a) a source of a beam of electromagnetic radiation;
   b) polarization state generator components;
   c) polarization state analyzer components;
   d) a detector of electromagnetic radiation;
such that in use a beam of electromagnetic radiation from the source of a beam of electromagnetic radiation is caused to pass through said polarization state generator components and then continue on to interact with said a sample, then pass through the polarization state analyzer components and enter said detector of electromagnetic radiation, wherein data is produced which can be analyzed to characterized the sample;
said combined environmental chamber and ellipsometer system being distinguished in that the polarization state generator and/or polarization state analyzer components are present inside at least one encasement which at least one encasement is present inside said environmental chamber, and in that the at least one encasement present inside said environmental chamber supports an environment internal thereto which is different from that inside the environmental chamber in which it is present.

2. A system as in claim 1, which comprises two encasements inside said environmental chamber, one of which contains polarization state generation components and another of which contains polarization state analyzer components.

3. A system as in claim 1, in which said source of a beam of electromagnetic radiation and said detector of electromagnetic radiation provide and receive, respectively, electromagnetic radiation to and from said polarization state generator and polarization state analyzer components, respectively, via fiber optics through at least one sealed port coupler in said environmental chamber.

4. A system as in claim 1, in which at least one of said polarization state generation components and/or said polarization state analyzer components are electrically operated, and wherein electrical energy is provided thereto through at least one sealed port coupler in said environmental chamber.

5. A system as in claim 4, in which there are separate sealed port couplers present for optical fibers and electrical energy transmitting wires for said polarization state generation components and/or said polarization state analyzer components.

6. A system as in claim 1, wherein said at least one encasement present inside said environmental chamber allows for "Z", and "X" and/or "Y" motion over an area of said sample, and said sample being investigated is movable in the "Y" and/or "X" direction respectively, thereby allowing for sample mapping at a multiplicity of "X" and/or "Y" locations on said sample, where "Z" indicates a distance between said sample and said polarization state generation and said polarization state analyzer components.

7. A system as in claim 1, wherein said polarization state generator components and polarization state analyzer components each comprise a polarizer.

8. A system as in claim 1, wherein said polarization state generator components and polarization state analyzer components each comprise a polarizer and at least one thereof also comprises a compensator.

9. A method of mapping a sample comprising the steps of:
   a) providing a combined environmental chamber and ellipsometer system, wherein the ellipsometer system comprises:
      a') a source of a beam of electromagnetic radiation;
      b') polarization state generator components;
      c') polarization state analyzer components;
      d') a detector of electromagnetic radiation;
such that in use a beam of electromagnetic radiation from the source of a beam of electromagnetic radiation is caused to pass through said polarization state generator components and then continue on to interact with a sample, then pass through the polarization state analyzer components and enter said detector of electromagnetic radiation, wherein data is produced which can be analyzed to characterized the sample;
said combined environmental chamber and ellipsometer system being distinguished in that the polarization state generator and polarization state analyzer components are present inside at least one encasement which encasement is present inside said environmental chamber, and in that the at least one encasement present inside said environmental chamber supports an environment internal thereto which is different from that inside the environmental chamber in which it is present;
said system providing that said at least one encasement present inside said environmental chamber allows for "Z", and "X" and/or "Y" motion over an area of said sample, and said sample being investigated is movable in the "Y" and/or "X" direction respectively, thereby allowing for sample mapping at a multiplicity of "X" and/or "Y" locations on said sample, where "Z" indicates a distance between said sample and said polarization state generation and said polarization state analyzer components;

b) for each of a plurality of "X", "Y" and "Z" values causing a beam of electromagnetic radiation from said source of a beam of electromagnetic radiation to pass through said polarization state generator components and then continue on to interact with said sample, then pass through the polarization state analyzer components and enter said detector of electromagnetic radiation, wherein data is produced which can be analyzed to characterized the sample; and c) for each of said plurality of "X", "Y" and "Z" values analyzing the data produced by said detector to provide insight to said sample at a multiplicity of mapped locations thereon.

10. A method as in claim 9, in which the polarization state generator components are present in one encasement and the polarization state analyzer components are present in another encasement, which encasements provide an environment therewithin that is different from that in the environmental chamber.

\* \* \* \* \*